US011097243B2

(12) United States Patent
Huang et al.

(10) Patent No.: US 11,097,243 B2
(45) Date of Patent: Aug. 24, 2021

(54) SYSTEM AND METHOD OF DEHYDROGENATIVE COUPLING

(71) Applicant: King Abdullah University of Science and Technology, Thuwal (SA)

(72) Inventors: Kuo-Wei Huang, Thuwal (SA); Zhiping Lai, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 93 days.

(21) Appl. No.: 16/670,243

(22) Filed: Oct. 31, 2019

(65) Prior Publication Data

US 2020/0070117 A1    Mar. 5, 2020

Related U.S. Application Data

(62) Division of application No. 13/886,464, filed on May 3, 2013, now Pat. No. 10,500,559.
(Continued)

(51) Int. Cl.
*B01J 16/00* (2006.01)
*B01J 8/02* (2006.01)
(Continued)

(52) U.S. Cl.
CPC .............. *B01J 16/005* (2013.01); *B01J 8/009* (2013.01); *B01J 8/0257* (2013.01); *B01J 15/005* (2013.01);
(Continued)

(58) Field of Classification Search
CPC .. C07C 67/00; C07C 67/40; B01J 2531/0244; B01J 23/462
See application file for complete search history.

(56) References Cited

U.S. PATENT DOCUMENTS 3,450,500 A      6/1969  Setzer et al.
4,792,620 A  *  12/1988  Paulik .................. B01J 31/0231
                                                                560/232
(Continued)

OTHER PUBLICATIONS

Gunanathan et al, Journal of the American Chemical Society, Direct Conversion of Alcohols to Acetals and H2 Catalyzed by an Acridine-Based Ruthenium Pincer Complex, 2009, 131, pp. 3146-3147. (Year: 2009).*
(Continued)

*Primary Examiner* — Deborah D Carr
(74) *Attorney, Agent, or Firm* — Billion & Armitage

(57) ABSTRACT

Embodiments include a system that may include a reactor including a reaction zone and a gas release zone separated by a selectively permeable membrane, wherein the selectively permeable membrane permits hydrogen to pass through the membrane and substantially blocks a substrate and its dehydrogenative coupling product from passing through the membrane. Embodiments further include a method of producing a dehydrogenative coupling product, wherein the method may include exposing a substrate to a catalyst in a reaction zone of a reactor; coupling the substrate to form the dehydrogenative coupling product and hydrogen; and separating the hydrogen from the dehydrogenative coupling product using a selectively permeable membrane and passing the hydrogen to a gas release zone of the reactor.

11 Claims, 8 Drawing Sheets

Related U.S. Application Data

(60) Provisional application No. 61/643,258, filed on May 5, 2012.

(51) Int. Cl.
```
B01J 8/00      (2006.01)
B01J 23/46     (2006.01)
C07C 67/40     (2006.01)
B01J 31/18     (2006.01)
C07C 67/00     (2006.01)
B01J 15/00     (2006.01)
B01J 19/24     (2006.01)
```
(52) U.S. Cl.
CPC ......... *B01J 19/2475* (2013.01); *B01J 23/462* (2013.01); *B01J 31/189* (2013.01); *C07C 67/00* (2013.01); *C07C 67/40* (2013.01); *B01J 2219/00135* (2013.01); *B01J 2231/49* (2013.01); *B01J 2531/0244* (2013.01); *B01J 2531/821* (2013.01)

(56) References Cited

U.S. PATENT DOCUMENTS

| | | | |
|---|---|---|---|
| 5,189,201 | A | 2/1993 | Sano et al. |
| 5,449,848 | A | 9/1995 | Itoh |
| 8,598,351 | B2 | 12/2013 | Huang |
| 2007/0166206 | A1 | 7/2007 | Takahashi et al. |

OTHER PUBLICATIONS

Norskov et al, Nature Chemistry, Towards the Computational Design of Solid Catalysts, 2009, 1, pp. 37-46. (Year: 2009).*

Zhang et al, Journal of the American Chemical Society, Facile Conversion of Alcohols into Esters and Dihydrogen Catalyzed by New Ruthenium Complexes, 2005, 127, pp. 10840-10841. (Year: 2005).*

Lin et al, Catalysis Today, A study of ethanol dehydrogenation reaction in a palladium membrane reactor, 2004, 97, pp. 181-188. (Year: 2004).*

Campos-Martin, et al., "Hydrogen Peroxide Synthesis: An Outlook beyond the Anthraquinone Process", Angew. Chem. Int. Ed., 45, 2006, 6962-6984.

Chen, et al., "Ruthenium(II) pincer complexes with oxazoline arms for efficient transfer hydrogenation reactions", Tetrahedron Letters, 53, 2012, 4409-4412.

Colley, et al., "The detailed kinetics and mechanism of ethyl ethanoate synthesis over a Cu/Cr2O3 catalyst", Journal of Catalysis 236, Oct. 13, 2005, 21-33.

Gaspar, et al., "Chemicals from ethanol—The ethyl acetate one-pot synthesis", Applied Catalysis A: General 363, May 9, 2009, 109-114.

Gregory, et al., "The Production of Ethyl Acetate From Ethylene and Acetic Acid Using Clay Catalysts", Clay Minerals 18, 1983, 431-435.

Gunanathan, et al., "Direct Conversion of Alcohols to Acetals and H2 Catalyzed by an Acridine-Based Ruthenium Pincer Complex", J. Am. Chem. Soc. 131,, Feb. 13, 2009, 3146-3147.

He, et al., "Enhanced Reactivities toward Amines by Introducing an Imine Arm to the Pincer Ligand: Direct Coupling of Two Amines to Form an Imine Without Oxidant", Organometallics, 31, 2012, 5208-5211.

Inui, et al., "Direct Synthesis of Ethyl Acetate from Ethanol Carried Out under Pressure", Journal of Catalysis 212, 2002, 207-215.

Keuler, et al., "Comparing and modeling the dehydrogenation of ethanol in a plug-flow reactor and a Pd—Ag membrane reactor", Ind. Eng. Chem. Res., 41, 2002, 1960-1966.

Keuler, et al., "Developing a heating procedure to optimise hydrogen permencance through Pd—Ag membrances of thickness less than 2.2 micrometers", Journal of Membrane Science, 195, 2002, 203-213.

Keuler, "Dissertation: Optimising catalyst and membrane performance and performing a fundamental analysis on the dehydrogenation of ethanol and 2-butanol in a catalytic membrance reactor", Department of Chemical Engineering at the University of Stellenbosch,, Sep. 2000.

Keuler, et al., "The dehydrogenation of 2-butanol in a Pd—Ag membrance reactor", Journal of Membrane Science, 202, 2002, 17-26.

Lin, et al. "A stutdy of ethanol dehydrogenation reaction in a palladium membrane reactor", Catalysis Today, 97, 2004, 181-188.

Milstein, "Discovery of environmentally benign catalytic reactions of alcohols catalyzed by pyridine-based pincer Ru complexes, based on metal-ligand cooperation", Top Catal, 53, 2010, 915-923.

Nielsen, et al., "Towards a Green Process for Bulk-Scale Synthesis of Ethyl Acetate: Efficient Acceptorless Dehydrogenation of Ethanol", Angew. Chem., 124, 2012, 5809-5811.

Niwa, et al., "A One-Step Conversion of Benzene to Phenol with a Palladium Membrane", Science 295 (5552), Jan. 4, 2002, 105-107.

Ogata, et al., "Alkoxide Transfer from Aluminium Alkoxide to Aldehyde in the Tishchenko Reaction", Tetrahedron, vol. 25. Pergamon Press, 169, 929-935.

S'Anchez, et al., "Direct transformation of ethanol into ethyl acetate through catalytic membranes containing Pd or Pd—Zn: comparison with conventional supported catalysts", Green Chem., 13,, 2011, 2569-2575.

Santacesaria, et al., "Ethanol dehydrogenation to ethyl acetate by using copper and copper chromite catalysts", Chemical Engineering Journal 179, 2012, 209-220.

Shi, et al., "Direct H2O2 synthesis over Pd membranes at elevated temperatures", Journal of Membrane Science 348, 2010, 160-166.

Shu, et al., "Catalytic Palladium-based Membrane Reactors: A Review", The Canadian Journal of Chemical Engineering, vol. 69, Oct. 1991, 1036-1060.

Thomson, "The Antoine Equation for Vapor-Pressure Data", Chem. Rev. 38, 1946, 39 pages.

Zeng et al., "Impact of support mass flow resistance on low-temperature H2 permeation characteristics of a Pd95Ag5/Al2O3 composite membrane", Journal of Membrane Science 326, 2009, 681-687.

Zeng et al., "On alloying and low-temperature stability of thin, supported PdAg membranes", International Journal of hydrogen energy 37, Jan. 28, 2012, 6012-601999.

Zhang, et al., "Facile conversion of alcohols into esters and dihydrogen catalyzed by new ruthenium complexes", J. Am. Chem. Soc., 127, 2005, 10840-10841.

\* cited by examiner

SYSTEM AND METHOD OF DEHYDROGENATIVE COUPLING

CLAIM OF PRIORITY

This application is a divisional of U.S. application Ser. No. 13/886,464, filed on May 3, 2013, which issued as U.S. Pat. No. 10,500,559 on Dec. 10, 2019, which claims the benefit of prior U.S. Provisional Application No. 61/643,258, filed on May 5, 2012, which is incorporated by reference in its entirety.

TECHNICAL FIELD

This invention relates to methods and systems for dehydrogenative coupling.

BACKGROUND

A series of homogeneous and heterogeneous catalysts have been developed to catalyze a variety of dehydrogenation reactions, however, the use of the catalysts successfully in industry can require complicated processes in order to optimize production of certain products.

SUMMARY

A dehydrogenative coupling product can be produced by coupling a substrate to form a dehydrogenative coupling product and hydrogen and separating hydrogen from the dehydrogenative coupling product using a selectively permeable membrane. For example, green production of ethyl acetate and hydrogen from ethanol is achieved in nearly quantitative conversions and yields by utilizing a catalyst, such as dearomatized PNN-Ru(II) catalysts, in a membrane reactor, such as an ultrathin Pd—Ag alloy/ceramic membrane reactor. The coupling can be achieved without the need of acid or base promoters and hydrogen acceptors.

In one aspect, a method of producing a dehydrogenative coupling product can include exposing a substrate to a catalyst in a reaction zone of a reactor, coupling the substrate to form the dehydrogenative coupling product and hydrogen, and separating the hydrogen from the dehydrogenative coupling product using a selectively permeable membrane and passing the hydrogen to a gas release zone of the reactor.

In another aspect, a system for producing a dehydrogenative coupling product can include a reactor including a reaction zone and a gas release zone separated by a selectively permeable membrane, wherein the selectively permeable membrane permits hydrogen to pass through the membrane and substantially blocks a substrate and its dehydrogenative coupling product from passing through the membrane. The gas release zone can be configured to transport hydrogen out of the reactor. The reaction zone can surround the gas release zone. The selectively permeable membrane can be cylindrical.

In certain embodiments, the selectively permeable membrane includes a metal membrane on a solid support. The metal membrane can include palladium. The solid support can include a silicon oxide, aluminum oxide, titanium oxide, zirconium oxide, magnesium oxide, cerium oxide, zinc oxide, molybdenum oxide, iron oxide, nickel oxide, cobalt oxide, graphite, or stainless steel.

In certain embodiments, the substrate can be a low boiling point alcohol. The catalyst can be a homogeneous catalyst. The dehydrogenative coupling product can be an ester. The substrate and the catalyst can be substantially free of solvent.

In preferred embodiments, conversion of the substrate to the dehydrogenative coupling product is substantially quantitative.

Other features or advantages will be apparent from the following detailed description of several embodiments, and also from the appended claims.

DETAILED DESCRIPTION

Figure 1:
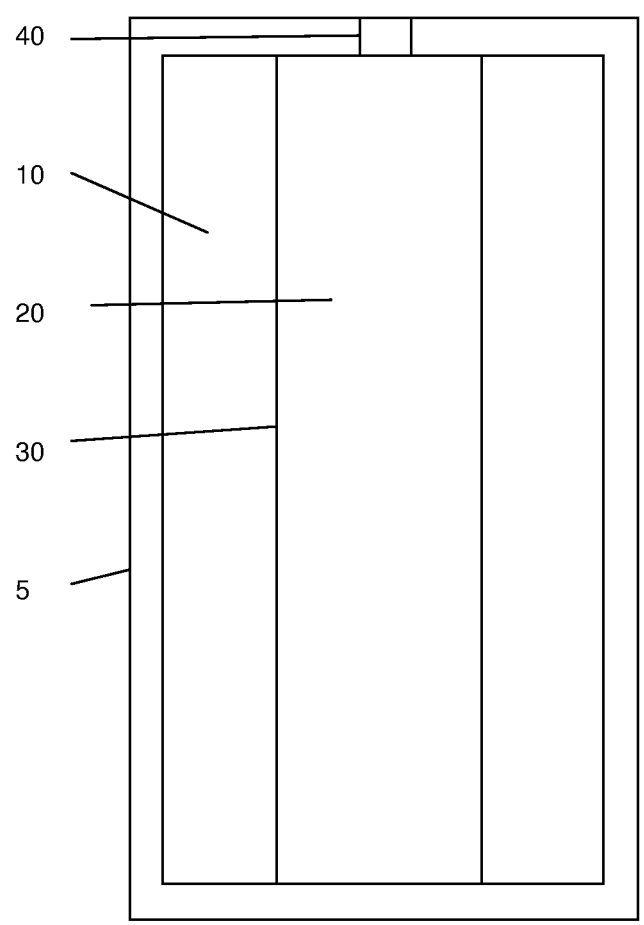
FIG. 1 is a schematic diagram depicting a system for dehydrogenative coupling.

A series of homogeneous and heterogeneous catalysts have been developed to catalyze a variety of dehydrogenation reactions such as dehydrogenative coupling of alcohols to esters, dehydrogenative coupling of alcohols and amines to amides and urea, dehydrogenation of alkanes to alkenes, dehydrogenative coupling of alkanes to higher homologs, etc. Examples are shown below.

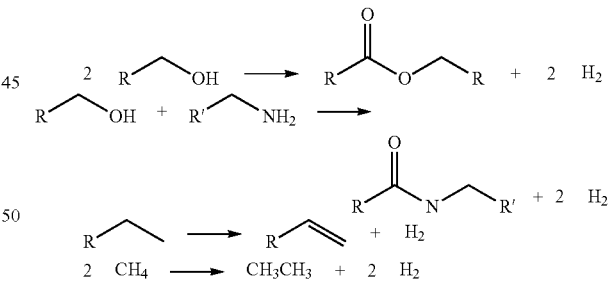

However, two major issues can limit the commercial development of the dehydrogenative processes. First, since the standard reaction temperature is in the range of 110-300° C., substrates with low boiling points (<100° C.) can be difficult to handle. Also, if the reactions are conducted in a traditional closed system (e.g. in a Parr reactor), the low yields were experienced due to the low conversion as the system reaches equilibrium.

The system and method described here is a process to design and utilize a metal membrane reactor such that the above mentioned reactions can be achieved in high yields and the valuable hydrogen byproduct can be separated and stored, or used as the alternative energy source to low down the energy consumption. The efficacy of this design has been fully examined with the following setup on dehydrogenative coupling of ethanol to ethyl acetate. In certain circumstances, over 99% conversion and yield can be achieved.

By way of example, industrial production of ethyl acetate is a highly energy intensive process which requires the reaction of ethanol and acetic acid in the presence of a strong acid ($H_2SO_4$) at 70% conversion followed by distillation. In the process described herein, dehydrogenative coupling of ethanol (b.p. 78° C.) can be achieved at 160-200° C. with quantitative conversion to ethyl acetate and two equivalent of hydrogen can be separated. This more economical process provides higher conversion and higher yield compared to current art. In general, membranes can now be used to design a reactor for dehydrogenation reactions of low boiling chemicals (<120° C.).

Ethyl acetate (EA) is an important industrial product employed in a wide range of applications from solvent to intermediates. See Ref. 1. In the industrial processes, EA is mainly produced via Fischer esterification of ethanol (EtOH) and acetic acid, and via Tishchenko reaction of acetaldehyde or addition of acetic acid to ethylene (Avada) on a smaller scale. See Refs. 2-5. These processes, in addition to the use of corrosive and/or toxic reagents/substrates, require energy-intensive distillation operations. Direct dehydrogenative coupling of EtOH to EA with the liberation of $H_2$ is therefore an attractive approach as it offers a simple, noncorrosive, relatively nontoxic and economic process. It only consumes EtOH, an inexpensive renewable raw material, as the feedstock, but provides EA and valuable hydrogen as the products. Many heterogeneous catalysts have been examined for this goal, yet most of them suffer from the low conversion rates and/or selectivity. See Refs. 6-10. As EtOH forms an azeotrope with EA at composition of 69.2%, separation of EA from the resulting EtOH mixtures is very challenging and energy-consuming. On the other hand, homogeneous catalysts have the potentials to achieve high conversion and selectivity, and in fact, a series of Ru pincer complexes have showed promising catalytic activities in the dehydrogenative coupling of primary alcohols to esters in high yields at 110-160° C. See refs. 11-12. However, extension of these reactions to alcohols with lower boiling points, such as ethanol and 1-propanol, still represents an issue due to the high reaction temperature needed.

PNN-Ru(II) complexes 1 and 3 show comparable catalytic activities towards dehydrogenation of primary alcohols to corresponding esters to that of Milstein catalyst 2 (Table 1). See Refs. 13, 14. Consistent with the literature results, when EtOH was employed, no reaction was observed after heating at reflux in the presence of 1 for 24 h. See Ref. 12. However, 69-75% conversions were achieved by carrying out the reactions in a pressure tube with 1-3, indicating that the pincer-Ru(II) catalysts indeed also work effectively for small alcohols when the reaction can be conducted at elevated temperatures. Since a closed system will be required to reach such a condition, we rationalize that the moderate conversions were due to the equilibrium reached: as the total pressure builds up because of the formation of $H_2$, the chemical equilibrium is backshifted.

$$2\ EtOH \rightarrow EA + 2H_2 \Delta rH_{198K}^\theta = 26\ kJ\ mol^{-1};$$

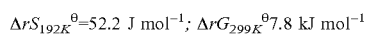

TABLE 1

Esterification of primary alcohol with PNN-Ru(II) complexes.[a]

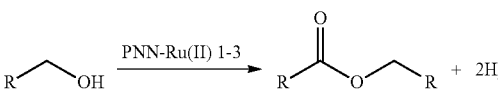

| Entry | R | Cat. | Cat. Loading (mol %) | T (° C.) | Conv. (%)[b] |
|---|---|---|---|---|---|
| 1 | $CH_3(CH_2)_4$– | 1 | 0.1 | 154 | 58 |
| 2 | $CH_3(CH_2)_4$– | 2 | 0.1 | 157 | 91.5[c] |
| 3 | Me | 1 | 0.5 | 78 | 0 |
| 4[d] | Me | 1 | 0.5 | 160 | 75 |
| 5[d] | Me | 2 | 0.5 | 160 | 75 |
| 6[d] | Me | 3 | 0.5 | 160 | 69 |

[a]Alcohol (5 mmol), suitable amount of ruthenium complex in a Schlenk flask equipped with a cooling finger are heated at the stated temperature under argon flow for 24 h;
[b]Determined by $^1$H NMR (>99% selectivity for EA formation);
[c]Ref. 11;
[d]the reaction were performed in 25 mL sealed tube under argon atmosphere.

From its thermodynamics, the formation of EA and $H_2$ is preferred at high temperature and under low pressure. Therefore, if the generated $H_2$ can be selectively in situ separated from the reaction mixtures, one will be able to drive the reaction to completion. In this regard, supported Pd-based composite membranes are the most applicable candidates for the selective hydrogen removal owing to their high and exclusive hydrogen permeability, high thermal stability, moderate chemical resistance and mechanical strength. Beller and co-workers just reported that up to 81% yield could be achieved for the dehydrogenation of EtOH to EA with the use of a more reactive Ru catalyst at 90° C. See Ref. 15. Considering the extreme difficulty in the separation of EtOH and EA, higher conversions and yields will be practically desirable. The design employs a defect-free ultrathin Pd—Ag/ceramic membrane reactor to overcome the above-mentioned issues to achieve quantitative conversion of EtOH to EA and $H_2$ without the use of solvent, acid or base promoters, or additional $H_2$ acceptors.

A method of producing a dehydrogenative coupling product includes catalytically coupling a substrate to form a dehydrogenative coupling product and hydrogen gas. The substrate can be an alcohol, in particular, a C1-C16 primary alcohol, a C1-C8 primary alcohol, or a C1-05 primary alcohol. Preferably, the alcohol can be a low boiling point alcohol having a boiling point of less than 250° C., less than 200° C., less than 150° C., or less than 100° C. Green and renewable alcohols, such as ethanol, propanol, butanol, etc., can be particularly attractive for use in this method. The dehydrogenative coupling product can be an alkyl ester of the alcohol, such as, for example, methyl formate, ethyl acetate, propyl propanoate, butyl butanoate, or pentyl pentanoate. In certain circumstances, the substrate can be a mixture of two or more alcohols. In other circumstances, the substrate and the catalyst can be substantially free of solvent, in which case the substrate serves as the solvent.

The catalyst can be a transition metal catalyst, such as a transition metal complex of, for example, ruthenium, nickel, iron, copper, cobalt, palladium, or platinum. The catalyst can be a homogeneous catalyst, such as a ruthenium(II) catalyst described in Nielsen, et al. Angew. Chem. Int. Ed. 2012, 51, or U.S. Provisional Patent Application No. 61/499,028, each of which is incorporated by reference in its entirety.

Importantly, the hydrogen can be separated from the dehydrogenative coupling product using a selectively permeable membrane. The hydrogen can then be passed into a gas release zone of the reactor and removed from the system. This process can assist in shifting the equilibrium of the coupling reaction to the coupled product, and can lead to nearly quantitative or quantitative conversion to product (e.g., 90%, 95%, 98%, 99%, 99.5% or higher completion). As a result, if highly pure starting materials are used, highly pure products are obtained. In certain circumstances, the products merely need to be removed from the catalyst by distillation, evaporation or filtration.

The selectively permeable membrane can include a metal membrane on a solid support. The membrane can be formed on the support or placed on the support. The metal membrane can include palladium. The selectively permeable membrane membrane permits hydrogen to pass through the membrane and substantially blocks a substrate and its dehydrogenative coupling product from passing through the membrane. In certain circumstances, the selectively permeable membrane allows hydrogen to pass, but not ethanol or ethyl acetate. Suitable membranes can be prepared, for example, by electroless plating. See Refs. 23-25.

The solid support can be a porous ceramic, for example, metal oxides, refractory oxides and molecular sieves, in particular from silicon oxides, aluminum oxides, zeolites, clays, titanium oxide, cerium oxide, magnesium oxide, niobium oxide, zinc oxide, molybdenum oxide, iron oxide, cobalt oxide, tantalum oxide or zirconium oxide, or a porous stainless steel structure, such as a metal frit, or mixtures thereof.

The method can be carried out at a selected temperature of about 300° C. or less, about 250° C. or less, about 200° C. or less, or about 180° C. or less. The method can be carried out at the pressure of the autogeneous saturation pressure of the liquid products between about 0.5 to 20 bar, or between about 1 and 10 bar.

Referring to FIG. 1, a system for producing a dehydrogenative coupling product can include a reactor 5 having a reaction zone 10 and a gas release zone 20 separated by a selectively permeable membrane 30. Reaction zone 10 can surround gas release zone 20. The gas release zone can be configured to transport hydrogen out of the reactor through port 40. The selectively permeable membrane can be cylindrical, columnar or have another long shape having a hollow interior region.

EXAMPLES

The following examples illustrate the systems and methods described herein, but are not meant to be limiting.

Preparation of Pd—Ag Membrane 35 mm long asymmetric $Al_2O_3$ membrane tubes were used as support, which has a mean surface pore size of 100 nm and inner and outer diameters of 7 and 10 mm (supplied by Inopor). After cleaning in ethanol the tubes were rinsed with deionized water, then soaked in 4% aqueous KOH solution and finally rinsed with DI water. Then the support was activated sequentially by seeding aqueous solutions ($PdSO_4$ 10 mmol/L, $EDTANa_2$ 1 mmol/L) at 60° C. and $N_2H_4$ dilute solution (20 mmol/L) at room temperature several times until the surface turned uniform dark grey. The Ag-controlled co-plating method was employed to prepare the Pd—Ag membrane. In a typical process, 60 mL Pd bath was loaded into a glass container and 15 mL Ag bath in a syringe. The Pd bath contained 3.9 mmol/L $PdCl_2$, 5 mol/L $NH_4OH$ and 0.12 mol/L $Na_2EDTA$ dissolved in deionized water, and the Ag bath contains 5.1 mmol/L $AgNO_3$, 5 mol/L $NH_4OH$, and 0.12 mol/L Na2EDTA mixed in deionized water. The activated support was vertically placed inside the Pd bath. Then, 0.45 ml $N_2H_4$ solution (1 mol/L) was added to the Pd bath and well mixed. Immediately, the Ag bath started to feed into the bottom of the Pd bath with the programming feeding rate (0.1 mL/min for 45 min and progressively decreased by 0.01 mL/min every 30 min interval). To achieve a defect-free membrane, the plating process above was conducted twice. After the first plating, the membrane was washed, dried and then annealed 10 h at 550° C. in $H_2$. Then the membrane was seeded again before the second co-plating, resulting in a 5 .mu.m thick $Pd_{75}Ag_{25}$ membrane. The final Pd—Ag membrane was heat-treated at 500° C. in $H_2$ for 36 h before used for reaction.

Characterizations of Pd—Ag Membrane

Figure 2:
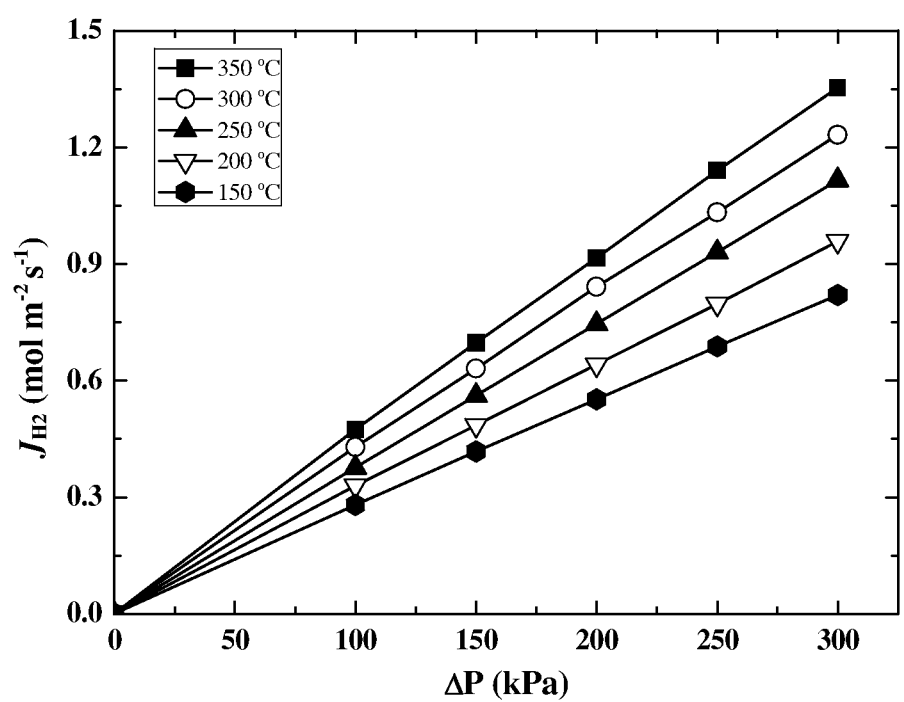
FIG. 2 is a graph depicting pressure dependence of $H_2$ flux of a Pd—Ag membrane at 150-350 K before reaction.
Figure 3:
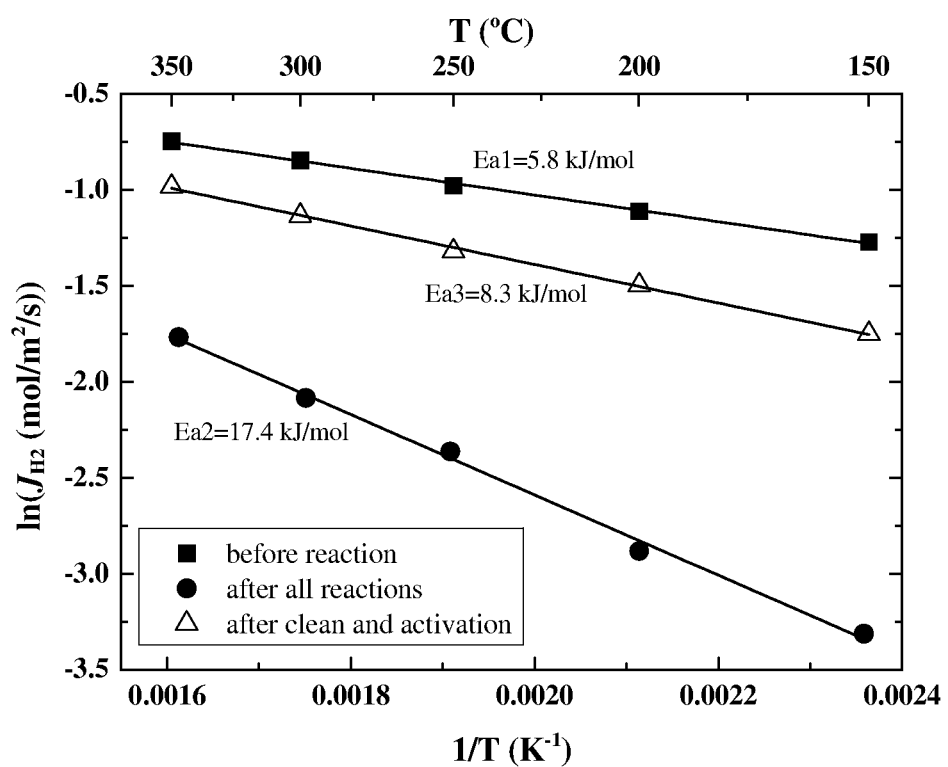
FIG. 3 is a graph depicting temperature dependence of $H_2$ flux of Pd—Ag membrane with $\Delta P_{H2}=100$ kPa.

The membranes were characterized by scanning electron microscopy (SEM, Quanta 600G, FEI) and energy-dispersive X-ray spectroscopy (EDX). The crystal structure and metal content of the alloy membranes were also determined by X-ray diffraction (XRD, Brokes) using Cu K.alpha. radiation with voltage set at 40 kV and current at 40 mA. For example, FIG. 2 shows the pressure dependence of $H_2$ flux of Pd—Ag membrane at 150-350 K before reaction. FIG. 3 shows the temperature dependence of $H_2$ flux of Pd—Ag membrane with $\Delta PH_{2=100}$ kPa.

Membrane Reaction

Figure 5:
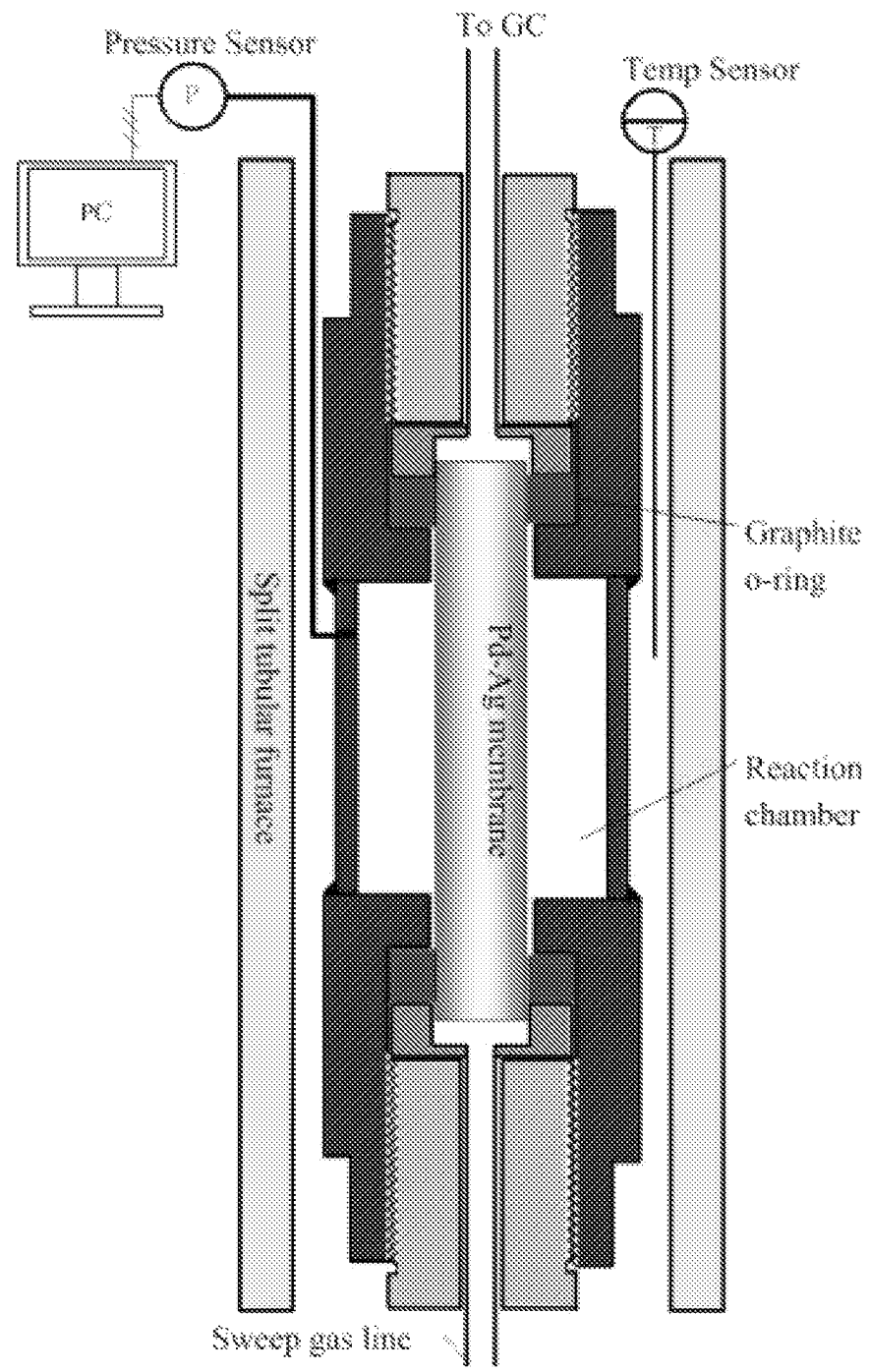
FIG. 5 is a schematic diagram depicting a system for dehydrogenative coupling.

The tubular alloy membrane was mounted in a custom-designed reaction cell, as shown in FIG. 5, with graphite gasket O-rings at both ends to reactor shell, which was placed inside a vertical furnace with programmable temperature controller. The reaction chamber had an effective membrane surface area of approx. 6 $cm_2$ and the volume of approx. 2 mL between the membranes and the shell of the cell, where the solution of EtOH and catalysts were contained. The reaction temperature was fixed on 160, 180 and 200° C., respectively, for different reactions. The membrane reactor was placed inside furnace after reaching the target temperature. 1 mL ethanol/PNN catalyst solution was fed into the space between outer surface of membrane and inner surface of reactor shell in the glove box. The actual feed side pressure was monitored and recorded each 20 sec with a pressure sensor on real-time at the retentate exit of the reactor. The liberated hydrogen in the permeance side of membrane was swept by constant flow rate Argon, with a typical volume flow rate of 200 mL/min, and the gas mixture was sequenced analyzed by one on-line GC (Agilent 7890A with PLOT/Q column) per 4 minute for the on-line composition analysis which allowed the hydrogen release rate to be calculated. The Pd membrane was washed with acetone and methanol several times and then dried at 100° C. after each reaction. The leakage of membrane with 0.8 MPa $N_2$ was checked by soap bubble meter (range 0-10 ml) before each reaction.

Figure 6:
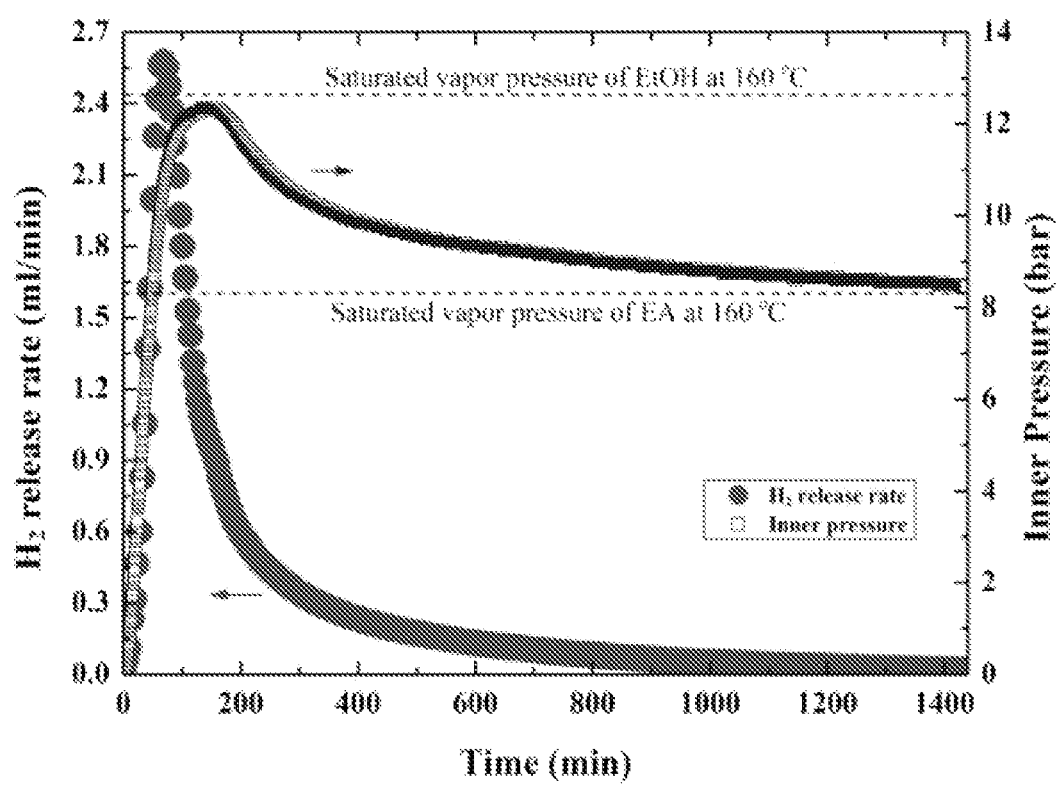
FIG. 6 is a graph depicting the hydrogen liberation rate and the total pressure of ethanol dehydrogenative coupling reaction at different reaction times at 436K.

In a typical reaction, 1 mL of EtOH and PNN-Ru(II) catalyst mixture was loaded into the chamber. The reaction was then monitored until completion. The hydrogen permeance and the membrane surface area in the design ensure the capability of the Pd—Ag membrane in fully removing the produced hydrogen during the course of the reaction. FIG. 6 shows the hydrogen release rate and the total pressure of the chamber at time interval of 20 sec during the reaction when the reaction was carried out at temperature of 160° C. The final conversion of EtOH and the yield of EA were analyzed by NMR and/or GC-MS. Moreover, it was also confirmed with the total pressure inside the reaction chamber as well as the total volume of the hydrogen released by integrating the hydrogen release curve in FIG. 6. Based on the assumption that there is no hydrogen accumulation in the system, the total pressure inside the reaction chamber will be determined only by the partial pressures of EtOH and EA according to the Raoult's law where x is the molar ratio of EtOH in the reaction mixture. See Ref. 24.

$$P = P_{EtOH}^{Sat} x + P_{EA}^{sat}(1-x)$$

Figure 7:
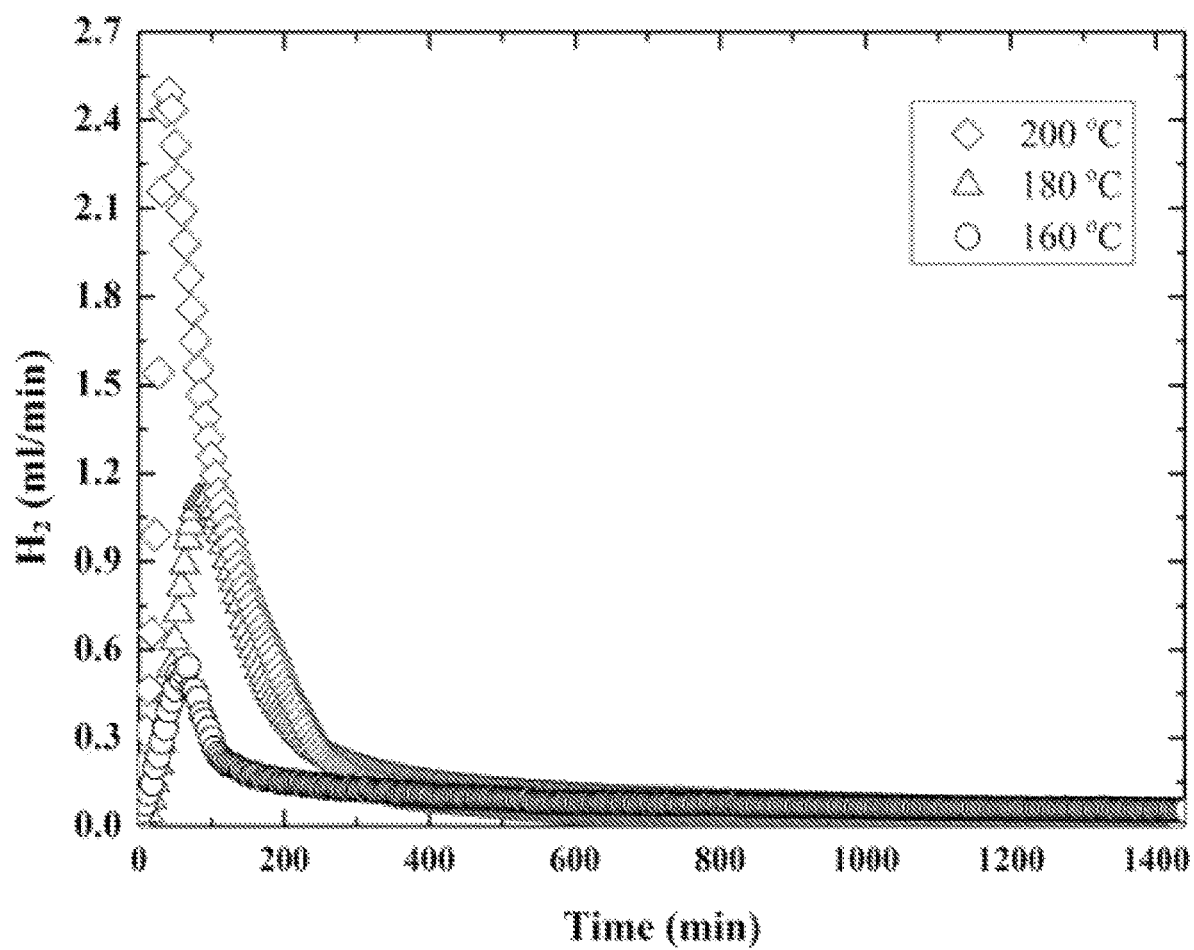
FIG. 7 is a graph depicting hydrogen fluxes of ethanol dehydrogenative coupling depending on the reaction temperature.
Figure 8:
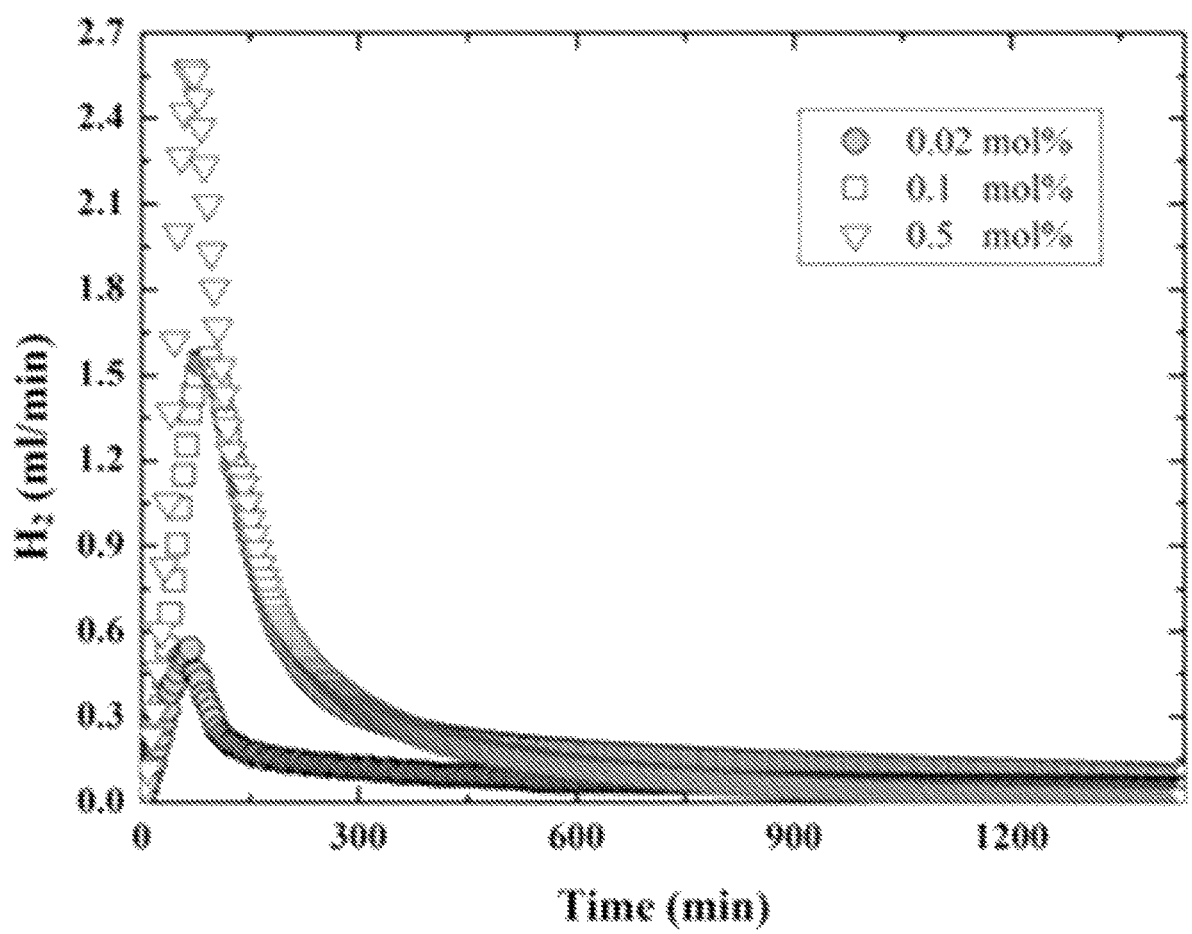
FIG. 8 is a graph depicting hydrogen fluxes of ethanol dehydrogenative coupling depending on the loading of catalyst at 160° C. over 24 hours.

Take the reaction at 160° C. for example, based on the NMR and GC-MS analyses, the EtOH conversion was .about.99% and the EA yield was .about.99% after 24 hours. The EtOH conversion calculated from the hydrogen release curve was 96%, while the total pressure indicated that the EtOH conversion was 98%. The influences of reaction temperatures and catalyst loadings on the conversion of EtOH were examined. The results are summarized in Table 2. The conversions of EtOH with 0.02 mol % of catalyst were found to increase with elevated temperatures, reaching 36, 57 and 65% at 160, 180 and 200° C., respectively (FIG. 7). Increasing the catalyst loading at 160° C. improved the conversion from 36% (0.02 mol %) to 96% (0.10 mol %) and eventually to 99% (0.50 mol %) (FIG. 7). As can be seen, conversions calculated from different means agree very well with one another, indicating that the Pd—Ag alloy membrane can timely remove hydrogen from the system, and more importantly, suggesting that in the membrane reactor system the progress of the reaction can be monitored. This may potentially serve as a powerful tool to study the reaction kinetics.

Figure 4:
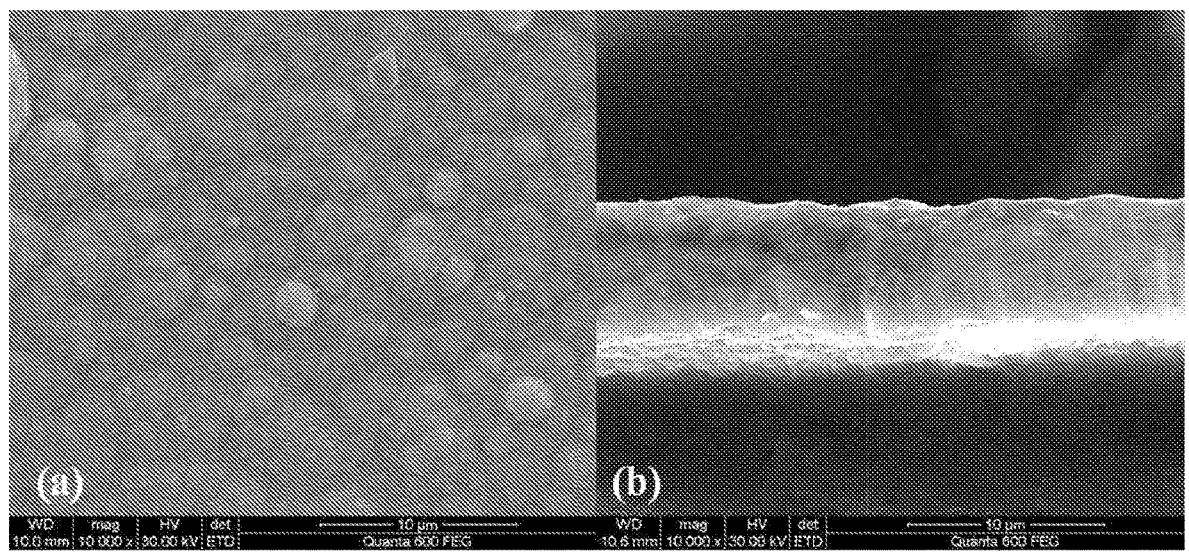
FIG. 4 are two photographs depicting scanning electron microscopy top view (a) and cross-section view of Pd—Ag membrane after reaction.

The mechanical strength of the Pd—Ag membrane was proved by the tolerability to high pressure of 10-30 bar during the temperature range of 150-200° C. The membrane also showed good performances in thermal stability and chemical resistance over more than 500 hours of service for this reaction system. $H_2$ and $N_2$ flux of the membrane was measured between 150-350° C. after all reactions were finished. No $N_2$ leakage of the membrane was detected at room temperature with $\Delta P=800$ kPa. However, the $H_2$ flux of Pd—Ag membrane at 350° C. with $\Delta P=100$ kPa was 0.17 mol m$^{-2}$ s$^{-1}$, ca. 37% of the fresh membrane. At the same time, the activation energy of $H_2$ permeation was increased from 5.8 to 17.4 kJ/mol. The observations of the decline of $H_2$ flux and increase of permeance resistance were believed to be caused by the physical adsorption of reagents and catalyst on the surface of the membrane. The performance can be recovered to 0.37 mol m$^{-2}$ s$^{-1}$ (77% of the fresh membrane with the activation energy of 8.3 kJ/mol) after being washed with methanol and annealed in $H_2$ at 500° C. for 48 hours (FIG. 3). The morphology measurement of the Pd—Ag membrane after reaction also showed no coking formed on the surface (FIG. 4). While EtOH may decompose to $CH_4$, CO and $H_2$ in the presence of Pd catalysts,[10] such reactions were not observed in the system as the inner pressure of the reactor was synchronously dropped to 0 when it was cooled to room temperature, indicative of no formation of other gases during the process.

TABLE 2

Dehydrogenative coupling of EtOH to EA and $H_2$ with PNN-Ru(II) complex 1 in a Pd—Ag membrane reactor.

| Entry | mol %[a] (×100) | T (° C.) | Conv. (%)[b] | Yield (%)[b] | Conv. $V_{H2}$[c] | $\Delta P$[d] |
|---|---|---|---|---|---|---|
| 1 | 1 | 200 | 25 | 98 | 22 | 27 |
| 2 | 2 | 160 | 36 | 98 | 33 | 40 |
| 3 | 2 | 180 | 57 | 99 | 59 | 60 |
| 4 | 2 | 200 | 65 | 99 | 66 | 68 |
| 5 | 10 | 160 | 96 | 99 | 94 | 93 |
| 6 | 50 | 160 | 99 | 99 | 96 | 98 |

[a]PNN-Ru(II) complex 1.
[b]Determined by $^1$H NMR and GC/MS.
[c]Determined by $H_2$ produced.
[d]Determined by the total pressure inside the reaction chamber.

In summary, that quantitative production of ethyl acetate and hydrogen directly from EtOH can be achieved in an ultrathin Pd—Ag/ceramic membrane reactor. This environmentally benign reaction is homogeneously catalyzed by dearomatized pincer Ru complexes, and no acid or base promoters and hydrogen acceptors are required. Defect-free Pd—Ag/ceramic membrane was employed for the in situ removal of the liberated hydrogen, allowing the reaction to be operated at elevated temperatures and reach almost 100% conversion and EA production yields. Furthermore, the liberated $H_2$ fluxes and the inner pressure of the reactor both can be used to accurately monitor the reaction progress in real-time.

REFERENCES

Each reference is incorporated by reference in its entirety.
1. K. Weissermel, H. Arpe, Industrial Organic Chemistry, 4th ed., VCH, Weinheim, 2003.
2. J. A. Monick, Alcohol, 1968, 19, 45.
3. Y. Ogata and A. Kawasaki, Tetrahedron, 1969, 25, 929.
4. R. Gregory, D. J. H. Smith and D. J. Westlake, Clay Minerals, 1983, 18, 431.
5. K. Sano, M. Nishiyama, T. Suzuki, S. Wakabayashi, K. Miyahara and K. K. Showa Denko, 1993, EP 0562139
6. K. Inui, T. Kurabayashi and S. Sato, J. Catal., 2002, 212, 207.
7. E. Santacesaria, G. Carotenuto, R. Tesser, M. Serio, Chem. Eng. J., 2012, 179, 209.
8. A. Gaspar, A. Esteves, F. Mendes, F. G. Barbosa, L. Appel, Appl. Catal. A: Gen., 2009, 363, 109.
9. S. Colley, J. Tabatabaei, K. Waughb, M. A. Wood, J. Catal., 2005, 236, 21.
10. A. Sanchez, N. Horns, S. Miachon, J. Dalmon, J. Fierro, P. Piscina, Green Chem., 2011, 13, 2569.

11. J. Zhang, G. Leitus, Y. Ben-David and D. Milstein, J. Am. Chem. Soc., 2005, 127, 10840.
12. C. Gunanathan, L. Shimon, D. Milstein, J. Am. Chem. Soc., 2009, 131, 3146.
13. T. Chen, L. He, D. Gong, L. Yang, X. Miao, J. Eppinger, K. Huang, Submitted.
14. L. He, T. Chen, D. Gong, K. Huang, Submitted.
15. M. Nielsen, H. Junge, A. Kammer, M. Beller, Angew. Chem. Int. Ed. 2012, 51.
16. J. Shu, B. Grandjean, A. Neste, S. Kaliaguine, Can. J. Chem. Eng., 1991, 69, 1036.
17. S. Niwa, M. Eswaramoorthy, J. Nair, A. Raj, N. Itoh, H. Shoji, T. Namba, F. Mizukami, Science, 2002, 295, 105.
18. J. Campos-Martin, G. Blanco-Brieva, J. Fierro, Angew. Chem., Int. Ed., 2006, 45, 6962.
19. L. Shi, A. Goldbach, G. Zeng, H. Xu, J. Membr. Sci., 2010, 348, 160.
20. J. Keuler, L. Lorenzen, Ind. Eng. Chem. Res., 2002, 41, 1960.
21. G. Zeng, A. Goldbach, H. Xu, J. Membr. Sci., 2009, 326, 681.
22. G. Zeng, Y. Liu, I. Pinnau, Z. Lai, Submitted.
23. G. Zeng, A. Goldbach, L. Shi, H. Xu, Int. J. Hydrogen Energ., 2012, 37, 6012.
24. G. Thomson, Chem. Rev., 1946, 38, 1

Other embodiments are within the scope of the following claims.

What is claimed is:

1. A method of producing a dehydrogenative coupling product, comprising:
    exposing a substrate to a catalyst in a reaction zone of a reactor, wherein the catalyst includes at least one of the following chemical structures:

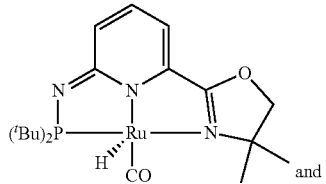
and
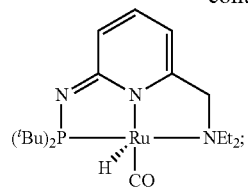

coupling the substrate to form the dehydrogenative coupling product and hydrogen; and
    separating the hydrogen from the dehydrogenative coupling product using a selectively permeable membrane and passing the hydrogen to a gas release zone of the reactor.

2. The method of claim 1, wherein the selectively permeable membrane includes a metal membrane on a solid support.

3. The method of claim 2, wherein the metal membrane includes palladium.

4. The method of claim 2, wherein the solid support includes a silicon oxide, aluminum oxide, titanium oxide, zirconium oxide, magnesium oxide, cerium oxide, zinc oxide, molybdenum oxide, iron oxide, nickel oxide, cobalt oxide, graphite, or stainless steel.

5. The method of claim 1, wherein the substrate is a C1-C16 primary alcohol, a C1-C8 primary alcohol, or a C1-C5 primary alcohol, or a mixture of two or more of said alcohols.

6. The method of claim 1, wherein the dehydrogenative coupling product is an ester.

7. The method of claim 1, wherein the dehydrogenative coupling product is an alkyl ester of an alcohol.

8. The method of claim 1, wherein the dehydrogenative coupling product is methyl formate, ethyl acetate, propyl propanoate, butyl butanoate, or pentyl pentanoate.

9. The method of claim 1, wherein the catalyst is a dearomatized PNN-Ru(II) catalyst.

10. The method of claim 1, wherein the substrate and the catalyst are free of solvent.

11. The method of claim 1, wherein the coupling proceeds in the absence of acid promoters, base promoters, hydrogen acceptors, or combinations thereof.

* * * * *